(12) United States Patent
Tuchfarber et al.

(10) Patent No.: US 10,451,623 B2
(45) Date of Patent: Oct. 22, 2019

(54) SYSTEM FOR CHEMILUMINESCENCE-BASED DETECTION OF METHICILLIN-RESISTANT STAPHYLOCOCCUS AUREUS

(71) Applicant: NanoDetection Technology, Inc., Franklin, OH (US)

(72) Inventors: William Tuchfarber, Amelia, OH (US); Douglas Harris, Cincinnati, OH (US); James Marous, South Vienna, OH (US)

(73) Assignee: NanoDetection Technology, Inc., Franklin, OH (US)

( * ) Notice: Subject to any disclaimer, the term of this patent is extended or adjusted under 35 U.S.C. 154(b) by 477 days.

(21) Appl. No.: 15/083,427

(22) Filed: Mar. 29, 2016

(65) Prior Publication Data

US 2017/0285026 A1 Oct. 5, 2017

(51) Int. Cl.
- *G01N 33/569* (2006.01)
- *B01L 3/00* (2006.01)
- *G01N 21/76* (2006.01)
- *G01N 33/558* (2006.01)
- *G01N 21/75* (2006.01)

(52) U.S. Cl.
CPC ...... *G01N 33/56938* (2013.01); *B01L 3/5023* (2013.01); *B01L 3/50273* (2013.01); *B01L 3/502715* (2013.01); *C12Y 111/01007* (2013.01); *G01N 21/76* (2013.01); *G01N 33/558* (2013.01); *B01L 2200/025* (2013.01); *B01L 2300/0663* (2013.01); *B01L 2300/0681* (2013.01); *B01L 2300/0867* (2013.01); *B01L 2400/0406* (2013.01); *B01L 2400/0481* (2013.01); *G01N 2021/752* (2013.01); *G01N 2021/757* (2013.01); *G01N 2333/31* (2013.01); *G01N 2333/908* (2013.01); *G01N 2469/10* (2013.01)

(58) Field of Classification Search
None
See application file for complete search history.

(56) References Cited

U.S. PATENT DOCUMENTS

| | | | | |
|---|---|---|---|---|
| 2006/0008847 A1* | 1/2006 | Ramel | ............... | B01L 3/5023 435/7.1 |
| 2008/0145835 A1* | 6/2008 | Alajem | ............ | B01L 3/5023 435/4 |
| 2011/0250202 A1* | 10/2011 | Cote | ............ | C07K 16/1271 424/135.1 |
| 2012/0282634 A1* | 11/2012 | Hughes | ........... | G01N 33/538 435/7.25 |

(Continued)

FOREIGN PATENT DOCUMENTS

WO   WO-2013033727 A1 * 3/2013   ........... G01N 33/558

*Primary Examiner* — Christine Foster

(57) ABSTRACT

The present disclosure comprises a device and accompanying method for determining the presence or absence of Methicillin-resistant *Staphylococcus aureus* in a sample. The disclosure includes the following elements: (1) a lateral flow strip for microfluidic manipulation of a sample; (2) a cassette device for containing the lateral flow strip and enabling interface with a detection device; (3) a cassette handler; (4) a luminous reagent delivery device; and (5) an electromagnetic radiation detection device capable of converting chemiluminescent radiation from the lateral flow strip into an output for a user.

6 Claims, 9 Drawing Sheets

(56) References Cited

U.S. PATENT DOCUMENTS

2013/0023444 A1* 1/2013 Kovalenko .............. C12Q 1/28
  506/12
2013/0330713 A1* 12/2013 Jakubowicz ..... G01N 35/00069
  435/5

* cited by examiner

SYSTEM FOR CHEMILUMINESCENCE-BASED DETECTION OF METHICILLIN-RESISTANT *STAPHYLOCOCCUS AUREUS*

CROSS-REFERENCE TO RELATED APPLICATIONS

The present application has specification that builds upon PCT/US12/053705, entitled "System for Chemiluminescence-based Detection," filed Sep. 4, 2012; the disclosure of which is hereby incorporated herein by reference in its entirety.

BACKGROUND OF THE INVENTION

Many existing systems and methods for detecting biological substances in a sample have disadvantages that make them unsuitable for use in many settings. Some of the known problems associated with current detection devices include their complexity, lack of sensitivity and/or specificity, and high cost. The detection of Methicillin-resistant *Staphylococcus aureus* ("MRSA") infection presents particular difficulty chiefly due to its similarity to more common strains of *Staphylococcus aureus* ("*Staph aureus*"). The ability to reliably distinguish MRSA from other forms of *Staph aureus* currently requires very precise and labor-intensive detection methods. For example, the CHROMagar™ test, which is used in 85-90% of current MRSA screens, involves placing a sample on a growth medium that is inoculated with a set amount of antibiotic. The growth medium is configured to impart a specific color to any type of *Staph aureus* colonies. If the appropriately colored bacteria are found growing on a specific portion of the plate, it is assumed that they must be MRSA due to their resistance to the antibiotic. The accurate interpretation of this test requires skilled subjective assessment of the color and growth pattern of cultivated samples. Further, the set amount of antibiotic may not be appropriate for all levels of MRSA infection, causing inaccurate test results in some cases. Other methods of MRSA detection, such as DNA-based detection, are expensive, i.e., $40 to $50 per test, and requiring a roughly $50,000 detection instrument; or, like the CHROMagar test, rely on the subjective interpretation skills of a user. Thus, there is a need for cost-effective, easy to use and accurate systems, methods and devices for analyzing biological samples for the presence of MRSA.

While detection of MRSA by chemiluminesent device, which is powered by a sensor integrated chip ("Sensor IC"), has the potential to address many of these problems, previous attempts to do so have failed. First, there is the difficulty of detecting MRSA itself. MRSA's similarity to other, less treatment-resistant forms of *Staph aureus* require the use of a specific biological capture agent. Further, MRSA is frequently present in the bodies of individuals without causing an infection, and therefore it is necessary to identify a detectible analyte that is indicative of an infection caused by MRSA. Accordingly, MRSA Penicillin Binding Protein 2a, which directly responsible for MRSA's resistance to antibiotic treatments, is a preferable analyte showing that a MRSA infection was actually established in the body.

In addition to selection of the proper analyte, previous attempts failed because of a lack of appreciation for the complexity of sample preparation necessary to use a chemiluminescent device. Previous methods did not address the development of room temperature stable formulations of reagents and capture antibodies necessary to simply and reliably extract the PBP2a and capture it for testing.

Previous methods also relied on manual application to the test strip of a luminous reagent, which is extremely difficult to meter with the necessary precision. Lack of consideration of the microfluidic challenges of the method also hindered the ability to ensure the proper speed and direction of sample and reagent flow across the reaction zone. In addition, previous Sensor IC systems, because of the extreme sensitivity of the detection device, were not robust. Namely, slight variations in technique by a user, or movement of the system caused insufficiently precise sample alignment with the Sensor IC diodes, and hence erroneous results. Significant improvements in the cassette device latching system and electromagnetic radiation apertures, as well as improvements to the cassette handler design were necessary to provide the necessary robustness to make a chemiluminescent system a viable testing platform. Finally, previous Sensor IC detectors did not provide diode calibration to ensure the needed accuracy to read a MRSA sample. Therefore the development of components and algorithms designed to calibrate the diodes was necessary to create a working system.

Before continuing with the background, a variety of definitions should be made, these definitions gaining further appreciation and scope in the detailed description and embodiments of the present invention.

Definitions

Antibody means all antibody molecules and fragments thereof, to the extent such fragments retain the binding properties of the intact molecule, including polyclonal and monoclonal preparations, and chimeric antibodies.

Chemiluminescence means the generation of light through an exothermic chemical reaction. For purposes of the present disclosure the chemical reaction is between a luminous reagent, and a protein marker that is bound via antibodies to an enzyme conjugate.

Enzyme conjugate means an oxidizing agent capable of binding with a target substance in a sample and reacting with a luminous reagent, thereby producing luminescence, e.g., horseradish peroxidase (HRP), alkaline phosphatase, beta-D galactosidase, glucose oxidase, or xanthine oxidase. The enzyme conjugate may be bound to an antibody to facilitate binding with the target substance. Other enzyme conjugates similar to those described above may also be used with the disclosed invention.

Human means individuals of the species *Homo sapiens*, without regard to a particular age or sex.

Luminous reagent means a compound that produces luminescence in the presence of an oxidizing agent, for example, luminol, diphenyl oxalate, or fluorescein. Other luminous reagents similar to those described above may also be used with the disclosed invention.

Protein marker means a peptide or protein that may be used to indicate the presence or absence of a target substance in a sample. A peptide or protein means a molecule comprising two or more amino acids joined to each other in a linear chain by peptide bonds, and refers to both short chain molecules, e.g., peptides, oligopeptides and oligomers, and to longer chain molecules, e.g., proteins.

Sample means fluid taken from an individual for analysis by the disclosed invention, including, without limitation, nasal fluid, blood, aspirate, plasma, saliva, serum, sputum, sweat, or urine.

The numbers expressing quantities of ingredients used to describe and claim certain embodiments of the disclosure may be modified in some embodiments by the term "about." Accordingly, in some embodiments, the numerical parameters set forth herein are approximations that can depend upon the desired properties sought in a particular embodiment. In other embodiments, the numerical quantities should be construed in reference to the reported significant digits and by applying ordinary rounding techniques.

Unless defined otherwise, technical and scientific terms used herein have the same meaning as commonly understood by one of ordinary skill in the art to which this invention belongs.

This has served as a background for the disclosed invention, including background technical information needed to fully appreciate the disclosed invention, which will now be summarized.

SUMMARY OF THE INVENTION

The present disclosure comprises a device for determining the presence or absence of Methicillin-resistant *Staphylococcus aureus* in a sample. The disclosure includes a lateral flow strip, which is comprised of four regions that are in fluid communication. These include (1) a first region for accepting a liquid sample; (2) a second region for accepting luminol, a luminous reagent; (3) a third region including a reaction zone, wherein the reaction zone is comprised of the following elements: (i) a substance binding region that includes a monoclonal MRSA PBP2a antibody for binding the PBP2a; (ii) a negative (blank) control region; and (iii) a positive control region that includes an anti-mouse IgG antibody, which is a means for trapping the HRP. The HRP is capable of binding with the protein marker substance, here MRSA PBP2a, and reacting with the luminol, thereby generating electromagnetic radiation. Finally, the lateral flow strip includes (4) a fourth region including a microfluidic pump. In some embodiments, one or more of the first through fourth regions are partially or completely overlapping.

The disclosure also includes a cassette device, which is comprised of a housing, which includes an upper component and a lower component configured to mechanically latch together, wherein (1) the upper component includes two hemispherical basins for sample preparation, a first well for adding a sample and a second well for adding a luminous reagent; (2) the lower component includes a region upon which the lateral flow strip rests; and (3) the first and second wells are in fluid communication with the lateral flow strip. The cassette device further includes three apertures on the upper component for allowing the electromagnetic radiation generated at the substance binding region and/or the control regions to escape from the device. The cassette's lower component also includes four indentations configured to mechanically interact with a complimentary structure on a cassette handler. The cassette device further includes a means for identifying the cassette device, such as RF, optical, barcode, QR barcode or combinations thereof.

The disclosure also includes a cassette handler, including a cassette acceptor, including an upper side and a lower side; a plurality of spring-loaded hemispherical ball plungers for securing a cassette into a predetermined position; and an aperture configured on the upper side of the cassette acceptor.

The disclosure also includes a luminous reagent delivery device, including a precise luminol metering means, and a transport means to deliver luminol to the luminol channel and well in the cassette device and onto the lateral flow strip region in precise amounts.

The disclosure also teaches an electromagnetic radiation detection device capable of converting chemiluminescent radiation from the reaction zone of the lateral flow strip into an electrical signal and ultimately into output for a user. The detection device is comprised of: (a) a housing, including an aperture; (b) a cassette handler, wherein the cassette handler is configured to fit into the housing and wherein at least a portion of the aperture of the housing is configured to align with at least a portion of the aperture of the cassette handler; (c) a luminous reagent delivery device; and (d) a self-calibrating sensor integrated chip ("Sensor IC") radiation detector that includes a discrete detection region. The detection device further includes a printer output for communicating data regarding the sample based on the detected radiation, and a display screen to facilitate operation.

In addition to the overall system, each of the individual components described herein offers important advantages over those used in conjunction with existing systems, as well as previous attempts to use a Sensor IC radiation detector to detect MRSA, as described in greater detail below.

BRIEF DESCRIPTION OF THE DRAWINGS

The objects and advantages of the present disclosure will be further appreciated in light of the following detailed descriptions and drawings in which:

FIG. 2(*b*) is an example embodiment of at least a portion of the present disclosure including a top view of the upper portion of a cassette device comprising an upper housing 201*b*, two hemispherical sample preparation basins labeled "A" 202*b*, and "B" 203*b*, a sample well labeled "C" 204*b*, three apertures 205*b*, 206*b*, and 207*b*, a reference line window 208*b*, a luminol channel 209*b*, a luminol well 210*b*, and four snap closure receptacle areas 211*b*.

FIG. 2(*c*) is an example embodiment of at least a portion of the present disclosure including an underside view of the upper portion of a cassette device comprising an upper housing 201*c*, a region 212*c* for mechanically interacting with the lateral flow strip (not shown). The region 212*c* is comprised of the following: a tab 213*c* for pushing the sample acceptor pad into the sample reservoir 203*d*; a three sided structure 214*c* around the sample window; a strip alignment region 215*c*; a strip pressure tab 216*c*; an aperture shield 217*c*; a luminol well nipple 218*c*; a microfluidic pump pressure tab 219*c*; and a microfluidic pump platform 220*c*.

FIG. 2(*d*) is an example embodiment of at least a portion of the present disclosure including a top view of the lower portion of a cassette device comprising a lower housing 201*d*, a region 212*d* for mechanically interacting with the lateral flow strip (not shown). The region 212d is comprised of the following: a fluid sample reservoir 203d; a lateral flow strip platform 204d; a set of upstream lateral flow strip alignment tabs 205d; and a set of downstream lateral flow strip alignment tabs 206d. The lower housing also has four snap closure latches 211d.

DETAILED DESCRIPTION OF THE INVENTION

The detailed description of the present disclosure will be primarily be, but not entirely be, limited to subcomponents, subsystems, and sub methods of detecting Methicillin-resistant *Staphylococcus aureus* ("MRSA") in a human using chemiluminescence. Therefore, although not described in detail here, other essential features which are readily interpreted from or incorporated along with the present disclosure shall be included as part of the present disclosure. The disclosed specification provides specific examples to portray inventive steps, but which will not necessarily cover all possible embodiments commonly known to those skilled in the art. For example, the specific invention will not necessarily include all obvious features needed for operation, examples being a battery or power source which is required to power electronics, or for example, a particular antenna design that allows wireless communication with a particular external information display device. The invention includes reference to PCT/US2012/053705, "System for Chemiluminescence-Based Detection," which is included herein by reference in its entirety. The disclosed invention may benefit from chemicals, materials, sensors, electronics, microfluidics, algorithms, computing, software, systems, and other features or designs, as commonly known to those skilled in the art of electronics, diagnostics, clinical tools, computing, and product design. Many of these auxiliary features of the device may, or may not, also require aspects of the disclosed invention.

Figure 1:
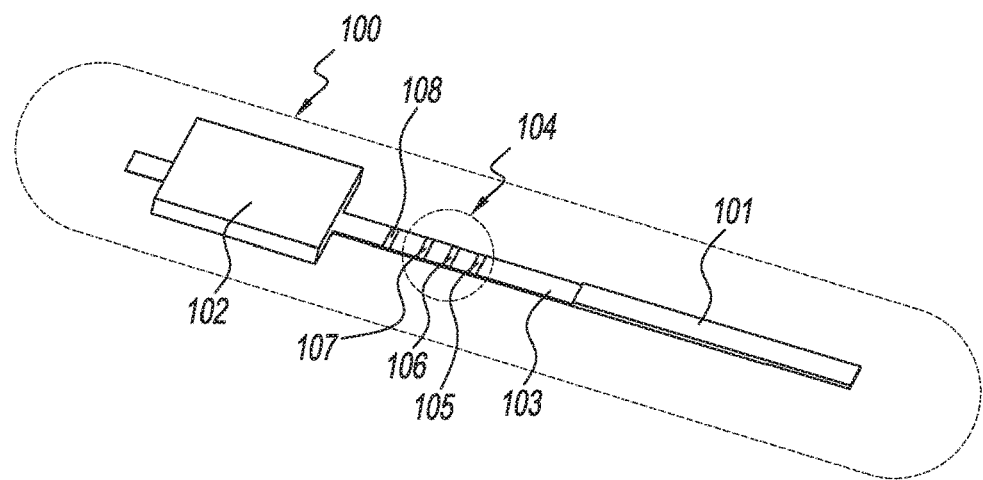
FIG. 1 is an example embodiment of at least a portion of the present disclosure including a lateral flow strip 100. The lateral flow strip is in fluid communication with a pad for accepting a liquid sample 101, and a microfluidic pump 102. The lateral flow strip comprises a region for accepting luminol 103, and a reaction zone 104. Within the reaction zone are a capture region 105, a negative control region 106 and a positive control region 107. The lateral flow strip also has an alignment reference line 108.

The disclosure teaches a cassette device for determining the presence or absence of MRSA in a sample. With reference to FIG. 1, the cassette device includes a lateral flow strip 100. The lateral flow strip is comprised of a water impermeable plastic backing and a nitrocellulose layer. For example, the lateral flow strip may be comprised of a Millipore cellulose ester membrane with a nominal thickness of 135 microns and width of 4.5 mm, direct cast onto a 4 mil polyester backing. The lateral flow strip has a nominal capillary flow rate of 90 seconds per 4 cm. The lateral flow strip 100 is in fluid communication with a sample acceptor pad 101 at an upstream end, and a microfluidic pump 102 comprising a pad with an absorbing volume of at least 600 µL at a downstream end. This volume is sufficient to move the fluid sample from the acceptor pad 101, through the lateral flow strip 100 and into the pump 102. The sample moves at a specific flow rate that is calibrated to facilitate capture and binding of the sample, as well as allowing the detection device to read the sample result. The acceptor pad 101 volume is sufficient to absorb the prepared sample (around 250 µL), and the pump 102 has sufficient volume to absorb the luminol (around 500 µL), which acts to prevent those fluids from fouling the cassette.

Adjacent to the upstream end, the lateral flow strip 100 also includes a region 103 for accepting a luminous reagent, i.e. luminol. Downstream from and adjacent to the luminol accepting region 103, the lateral flow strip includes a reaction zone 104. The reaction zone comprises a capture region 105, a negative control region 106 and a positive control region 107. The capture region 105 contains a means for capturing the PBP2a. The means for capturing the MRSA PBP2a is an anti-MRSA PBP2a monoclonal antibody. The capture region's PBP2a antibody acts as a sandwich assay by binding with the PBP2a and another MRSA PBP2a antibody bound to the PBP2a (if any) in the sample fluid. When luminol is supplied to the test strip, any captured PBP2a conjugated with HRP will produce electromagnetic radiation, which the Sensor IC will interpret as indicating the presence of MRSA (assuming the test is otherwise valid). If no signal is generated from the capture region, the Sensor IC will interpret such a result as indicating the absence of MRSA in the sample, also assuming the test is otherwise valid.

The negative or blank control region 106 can be used to calibrate the test for background noise (electromagnetic radiation). The level of such background noise contribution to a positive signal read by the Sensor IC device can thereby be determined and accounted for. The positive control region 107 includes a means for trapping the HRP, and serves as a means to determine if the sample flowed down the strip. The means for trapping the HRP is an IgG antibody. The IgG antibody in the positive control region 107 acts as a sandwich assay, and binds another IgG antibody in the sample fluid that is bound to the HRP. If HRP is captured in the positive control region 107, electromagnetic radiation will be produced, which the Sensor IC device will interpret as a valid test. If a sample fails to flow to the positive control region 107, the Sensor IC will interpret the absence of a signal as an invalid test.

Downstream of the reaction zone 104, the lateral flow strip of the device disclosed herein also includes an alignment reference line 108. The alignment reference line 108 is oriented across the width of the lateral flow strip, and will appear in the reference line window 208b when the lateral flow strip is properly seated in the lower cassette housing 201d, and the upper cassette housing 201b is properly secured in place. All of the regions of the lateral flow strip described above are in fluid communication. If one or more of such regions are omitted, the remaining regions will remain in fluid communication. One or more of the regions described above may also be partially or completely overlapping.

Figure 2A:
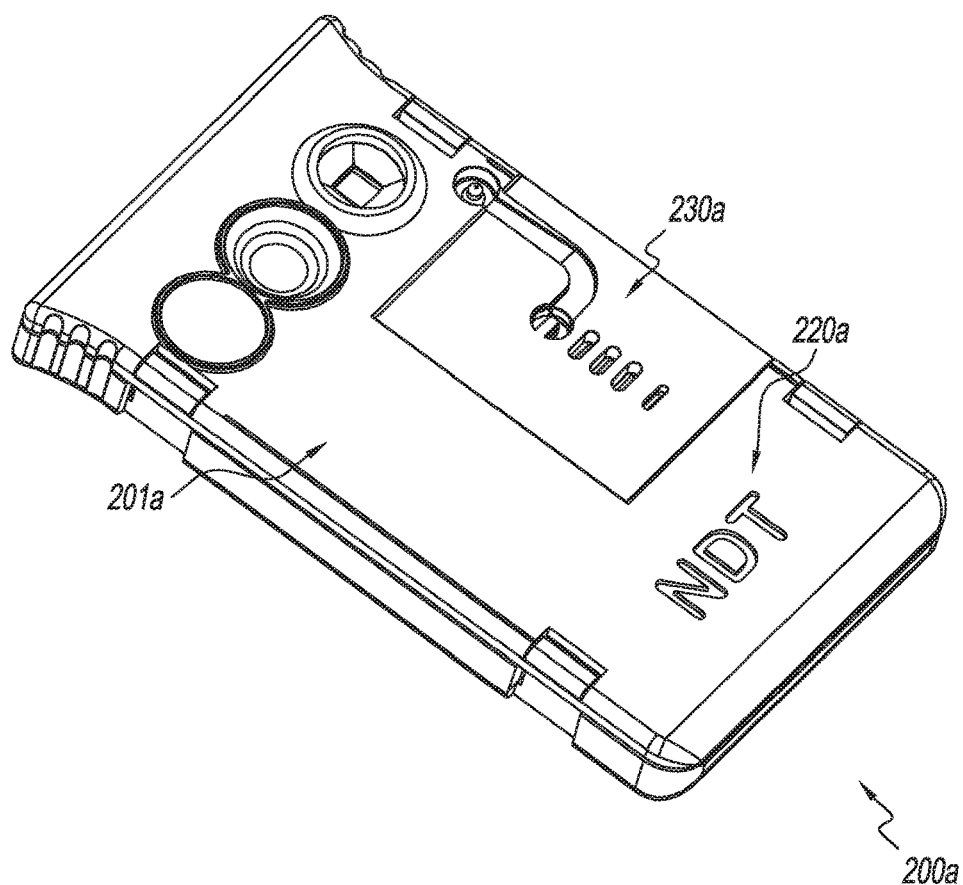
FIG. 2(*a*) is an example embodiment of at least a portion of the present disclosure including a cassette device 200*a* with a housing 201*a*, a region 220*a* configured to contain a means for cassette identification, and an area 230*a* that is covered with clear tape.
FIG. 2(e) is an example embodiment of at least a portion of the present disclosure including an underside view of the lower portion of the cassette device comprising a lower housing 201e and four hemispherical ball detents 202e.

With reference to FIG. 2a, the cassette device 200a includes a plastic housing 201a. The housing 201a is rectangular in shape having a length of about 91 mm, a width of about 56 mm, and an assembled height of about 10 mm. The housing 201a also includes region 220a where cassette identification means may be located. The means for cassette identification may include RF, optical, barcode, QR barcode, and combinations thereof. The identification region 220a may be located elsewhere on the cassette device so long as cassette device functions are not impaired. The housing 201a also includes a region 230a that is covered by clear tape.

As depicted in FIGS. 2(b) through 2(e), the cassette device 200 includes a housing 201. The cassette device includes an upper component, FIGS. 2(b) and 2(c), and a lower component FIGS. 2(d) and 2(e) that are configured to mechanically interact with one another. At the 56 mm sides of the housing, the housing has a first end that features a flanged area with ridges to improve handling by a device user, and a second end that features rounded corners. A user inserting the cassette device 200 into a Sensor IC reader device would grip the cassette by the first end and insert the second end into the cassette handler on the reader device.

The mechanical interaction between the upper component and the lower component is accomplished by means of four snap closures. The snap closures are located on the perimeter of the 91 mm sides of the cassette housing 201, and correspond roughly to the four corners of the housing. The snap closures are comprised of clips 211d projecting upward from the lower component, and complimentary latching areas 211b on the upper component. When properly latched, the four snap closures exert positive pressure that serves to: (1) secure the cassette housing components together, and (2) press the lateral flow strip together with the sample acceptor pad and the microfluidic pump.

Figure 2B:
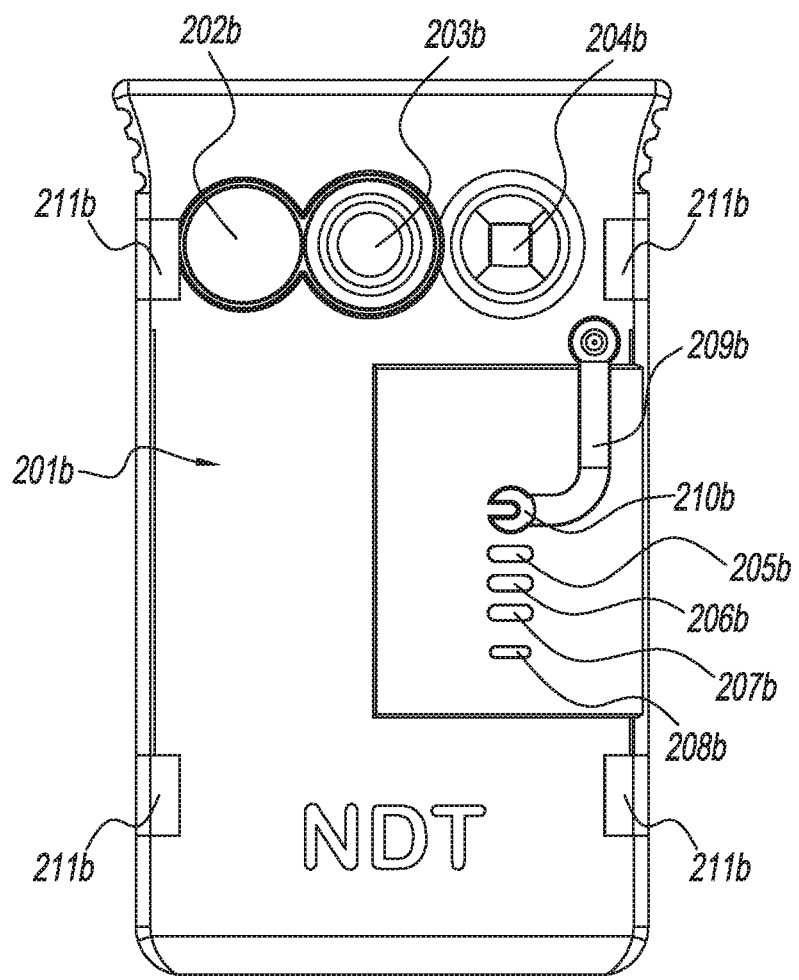

With reference to FIG. 2(b), the upper component includes two sample preparation basins "A" 202b, with an approximate volume of 222 µL, and "B" 203b, with an approximate volume of 289 µL, a well "C" for sample introduction 204b, a well for luminol introduction 210b and a channel for luminol transport 209b. The sample well 204b is in fluid communication with the lateral flow strip sample pad (FIG. 1, 101), while the luminol well 210b is in fluid communication with the luminol accepting region (FIG. 1, 103). The luminol channel 209b is a shallow channel for conveying luminol from the location that it is delivered to the cassette to the luminol well 210b. The luminol channel 209b has a reception area (not shown) where the luminol delivery system delivers the luminol to the cassette device. In the reception area, the luminol channel is configured with a hemispherical nipple that points upward from the cassette device. When a drop of luminol contacts the reception area, the nipple breaks the drop, allowing the luminol to flow down the luminol channel. Otherwise, the luminol drop would continue to grow larger and would eventually overflow the channel and foul the cassette device. The bottom and sides of the luminol channel 209b are treated with a surfactant, for example turgitol, that prevents the luminol from adhering to the channel, and facilitates flow to the luminol well 210b. Additionally, in region 230a, from FIG. 2(a), an optically clear tape is adhered to the cassette housing, sealing the top of the luminol channel 209b. Capillary action within the luminol channel facilitates luminol flow to the luminol well 210b. The luminol well 210b is configured as a circular opening of 2.1 mm diameter that is partially bisected by a tab having a rounded end and a hemispherical nipple (FIG. 2(c), 218c) pointing downward toward the lateral flow strip. When luminol is reaches the luminol well 210b, the disclosed nipple configuration causes the luminol to form a bubble that is pulled by capillary action onto the lateral flow strip in a thin, uniform layer.

Figure 2C:
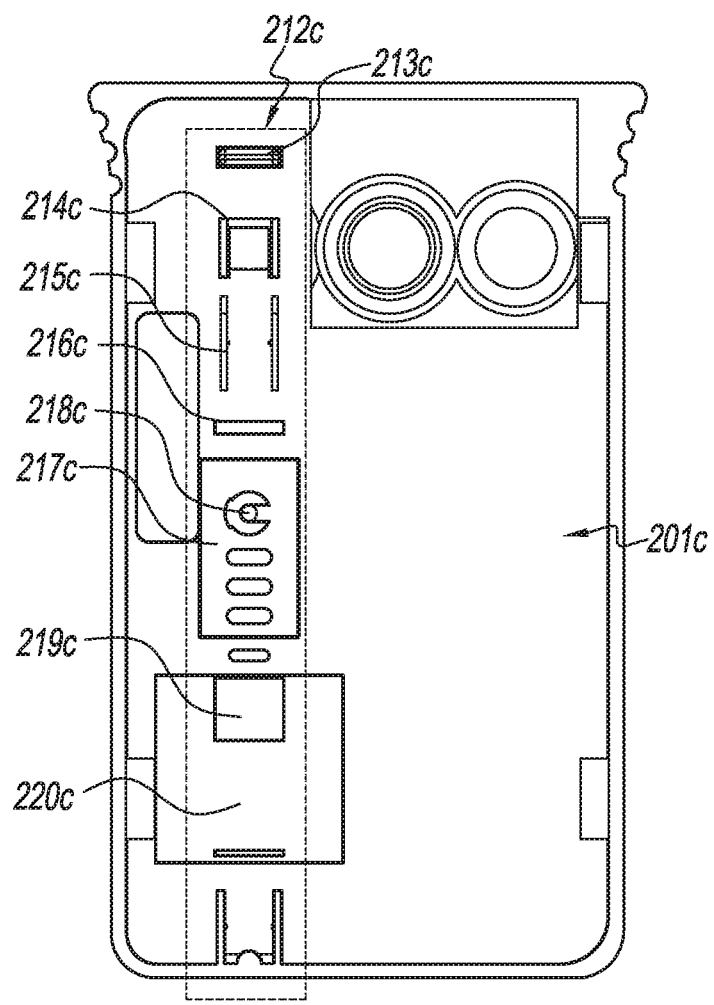

With reference to FIG. 2(c), the underside of the upper housing 201c includes a region 212c that interacts with the lateral flow strip. The region 212c includes a tab 213c that extends down perpendicularly toward the sample acceptor pad (FIG. 1, 101), and pushes the pad into a fluid sample reservoir (FIG. 2(d), 203d) situated on the lower component. Region 212c also includes a three-sided guide 214c configured around the sample well (FIG. 2(b), 204b) and extending down perpendicularly toward the sample acceptor pad, with the open side on the downstream side of the sample acceptor pad. The guide 214c directs sample flow downstream on the lateral flow strip. The region 212c also includes a set of lateral flow strip alignment guides 215c that correspond with similar guides configured on the lower cassette housing. Region 212c further includes tab 216c that extends down perpendicularly toward the lateral flow strip (FIG. 1, 100), and holds the strip against the sample acceptor pad with precise pressure to facilitate fluid flow at the required sample flow rate. The region 212c further includes a microfluidic pump pressure tab 219c and a microfluidic pump platform 220c that extend down perpendicularly toward the microfluidic pump (FIG. 1, 102), and hold the pump in place with precise pressure.

Figure 2D:
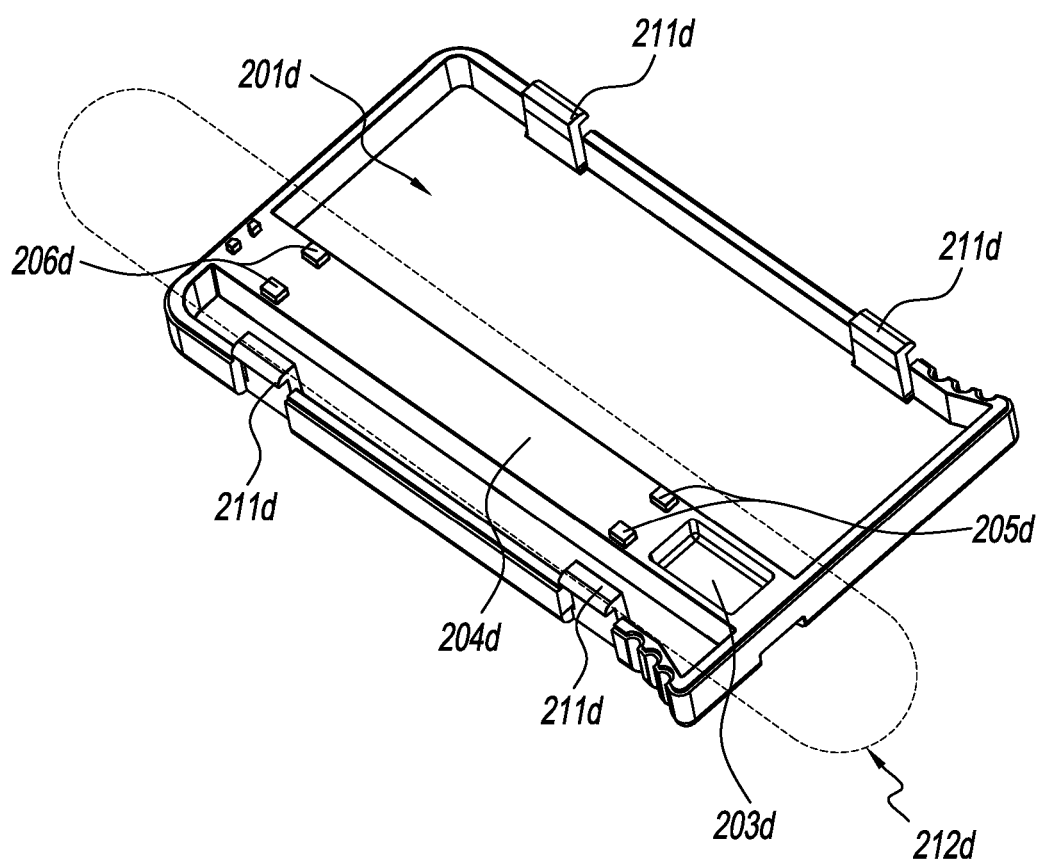
Figure 2E:
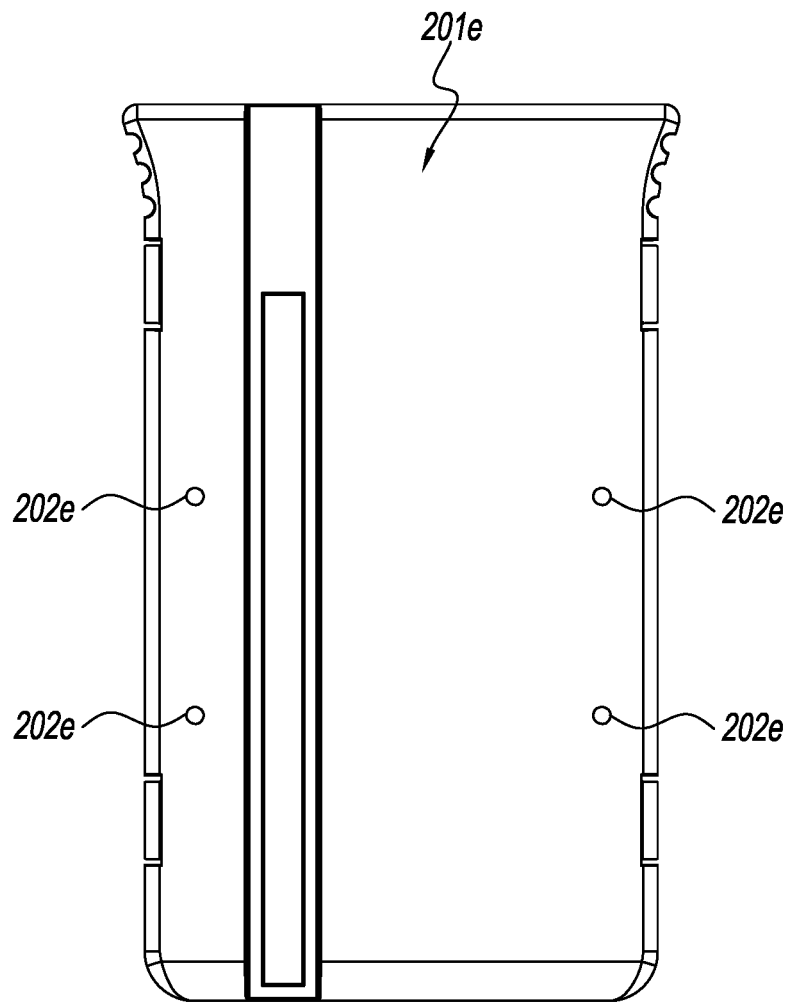

With reference to FIG. 2(d), the top of the lower cassette housing 201d includes a region 212d that interacts with the lateral flow strip 202d. The flow strip region 212d comprises a sample reservoir 203d, of approximately 245 µL volume, a platform 204d upon which the lateral flow strip rests, a set of upstream lateral flow strip alignment tabs 205d that extend upward perpendicularly and interact with alignment tabs on the upper housing (FIG. 2(c), 215c), a set of downstream lateral flow strip alignment tabs 206d that extend upward perpendicularly and serve to hold the lateral flow strip in place relative to apertures (FIGS. 2(b), 205b, 206b, and 207b).

The lower cassette housing 201d also includes four snap closure latches 211d. The snap closure latches 211d engage the complimentary latching areas (FIG. 2(b), 211b) on the upper housing with a positive clamping force of approximately 2.5 ounces per latch, which causes the various disclosed pressure tabs and structures to apply pressure to the lateral flow strip, sample acceptor pad and microfluidic pump to facilitate and precisely control fluid flow. This pressure facilitates fluid flow from the sample acceptor pad, across the lateral flow strip reaction zone, and to the microfluidic pump at the required flow rate. Further, the secure closure improves the robustness of the test by providing exact alignment among the reaction zone, the apertures, and the Sensor IC reader device that can tolerate the reader device being bumped or moved.

With further reference to FIG. 2(b), the cassette device 200b is configured to facilitate the transmission of electromagnetic radiation from the lateral flow strip reaction zone to the Sensor IC radiation detector. The upper cassette housing 201b includes three apertures 205b, 206b, and 207b, for allowing the electromagnetic radiation generated at the substance binding region and/or the control region to escape from the cassette device 200b. The apertures are arranged along the lateral flow strip and have a 4.5 mm side that spans the width of the lateral flow strip and a 1.5 mm side perpendicular to the test strip. A first aperture 205*b* is located correspondent to the capture region (FIG. 1, 105) of the lateral flow strip. A second aperture 206*b* is located correspondent to the negative control region (FIG. 1, 106) of the lateral flow strip. A third aperture 207*b* is located correspondent to the positive control region (FIG. 1, 107) of the lateral flow strip. As depicted in FIG. 2*c*, the upper housing 201*c* also features a aperture shielding region 217*c* surrounding the apertures, that, in conjunction with the shape of the apertures, directs light escaping from the corresponding region of the lateral flow strip to the appropriate diode(s) on the Sensor IC detection device, and blocks such light from scattering to other diodes, which would thereby interfere with the device measurements.

Figure 3:
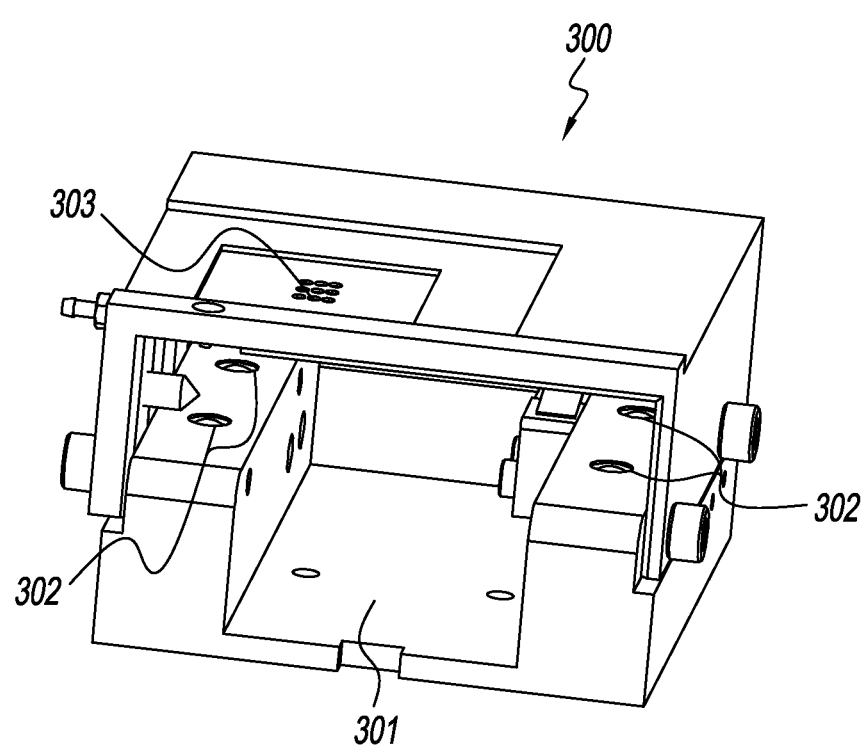
FIG. 3 is an example embodiment of at least a portion of the present disclosure including a cassette handler 300 with a cassette receiving component 301, four spring-loaded ball plungers 302, and an aperture 303.

As depicted in FIG. 2(*e*), the underside of the lower housing 201*e* of the cassette 200*e* includes four hemispherical ball detents 202*e* configured to mechanically interact with complimentary structures, such as the 3/16" diameter ball plungers 302 depicted on the cassette handler device 300 of FIG. 3. The ball plungers 302 are spring loaded by means of compression springs (not shown) capable of producing a compression rate of about 2.04 pounds/inch. One or more of the detents could be of a different shape, so long as they are configured to mechanically interact with one or more complimentary structures on a cassette handler. When the ball detents 202*e* interact with the cassette handler ball plungers 302, the three apertures 205*b*, 206*b*, and 207*b* will be aligned with the cassette handler aperture 303 so as to allow electromagnetic radiation generated at the lateral strip reaction zone to pass through the apertures 205*b*, 206*b* and 207*b*, through the cassette handler aperture 303, to the appropriate diode(s) of the Sensor IC detection device described herein. The Sensor IC detection device is so sensitive (i.e., each diode is able to detect as few as 200,000 photons/second) that even a small amount of cassette misalignment could cause light to scatter to an unintended diode, resulting in erroneous results. The disclosed configuration improves upon previous detection devices by providing a secure and precise alignment of the apertures that is robust enough to withstand deficiencies in cassette insertion or movement of the detection device. In addition, the ball plungers 302 improve ease of use by providing resistance to slow insertion speed, and by providing an audible and tactile positive snap in place when the cassette is properly seated in the cassette handler 300. The cassette handler device is mounted within the Sensor IC device at a 15 degree downward incline relative to a horizontal surface, which facilitates fluid flow within the cassette. With further reference to FIG. 3, the cassette handler 300 also includes a cassette receiving component 301; and an aperture 303 configured on the upper side of the receiving component 301. The aperture 303 prevents scattering of light to unintended diodes, which would cause erroneous results. The cassette handler may also include a hinged door, configured to substantially block the opening of the cassette acceptor (not shown). The hinged door is configured to close behind a cassette inserted into the cassette handler.

Figure 4:
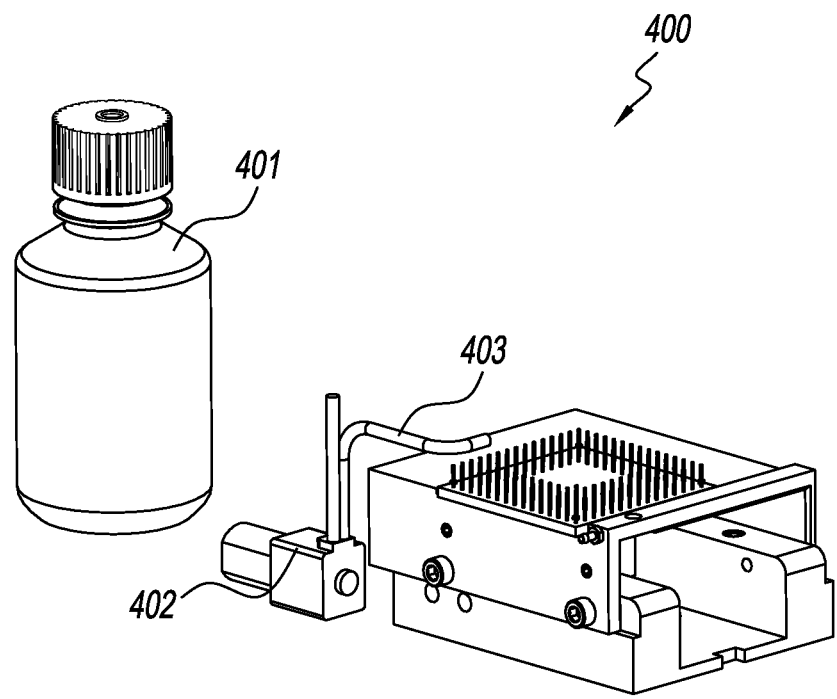
FIG. 4 depicts an example embodiment of the present disclosure including a Sensor IC detection device with a luminous reagent delivery device 400. The delivery device includes a container 401, a metering pump 402, and a delivery tube 403 for transferring the luminol from the container to the luminol channel 209b on the cassette device.

The electromagnetic radiation generated by a MRSA assay conducted using the cassette device described herein could be detected by using any appropriately configured Sensor IC detection device, including that described herein. In addition to the cassette handler disclosed above, the Sensor IC detection device also includes a luminous reagent delivery device. With reference to FIG. 4, the delivery device 400 includes a container 401 for storing the luminol, a metering pump 402, and a tube 403 for delivering the luminol to the luminol channel (FIG. 2(*b*), 209*b*) of the cassette device. The peristaltic metering pump 402 delivers discrete drops of luminol to the luminol well at a rate of 4 µL/sec. For each MRSA test conducted by the detection device, the delivery device 400 will supply a total of 400 µL of luminol. The delivery rate and minimum volume are critical for performing an accurate MRSA test using the device. If luminol is delivered in insufficient volume or rate, the positive control line will fail to produce electromagnetic radiation, and the test will be considered invalid. On the other hand, an excessive delivery rate or amount will cause fouling of the cassette device or will cause luminol to overflow the luminol channel.

Figure 5:
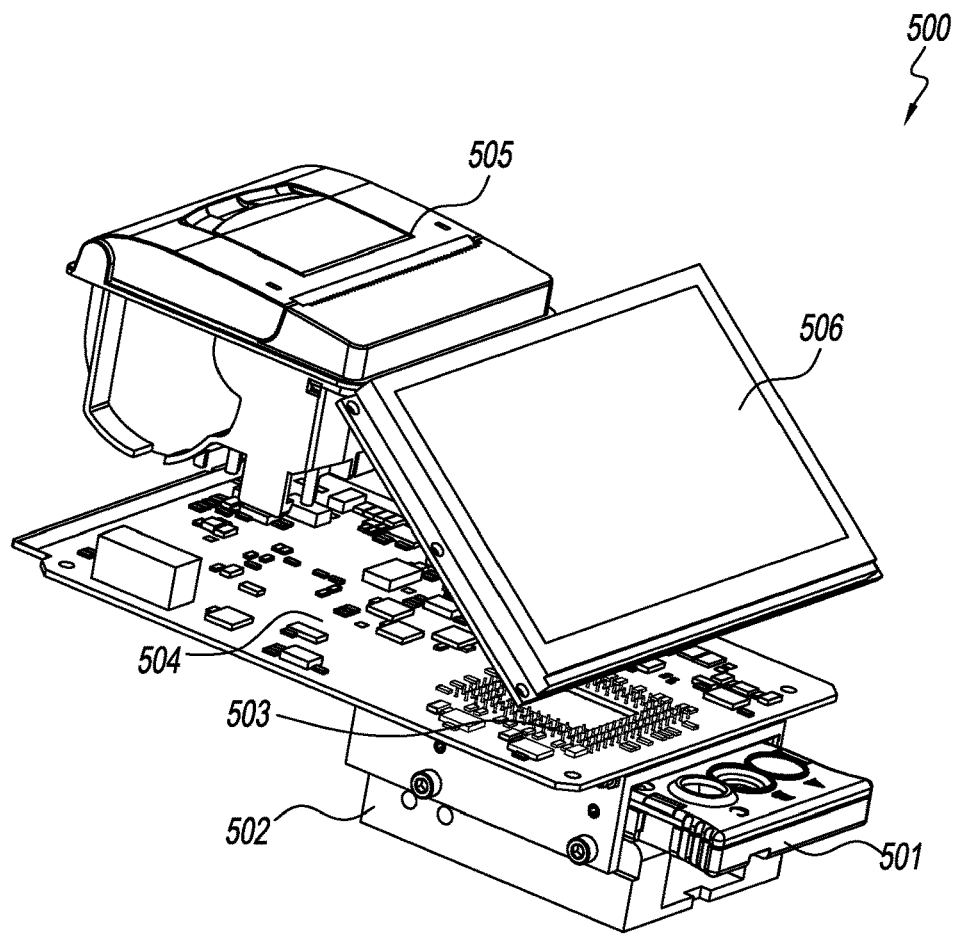
FIG. 5 depicts, in accordance with an embodiment of the disclosure, a view of a Sensor IC device 500 for detecting electromagnetic radiation on a cassette 501. The device includes a cassette handler 502, an aperture (not shown), a Sensor IC electromagnetic radiation detector 503, a plurality of signal processing printed circuit boards 504, a printer 505, and a user interface screen 506.

As depicted in FIG. 5, the disclosed Sensor IC electromagnetic radiation detection device 500 includes the following components: a cassette 501; a cassette handler 502; and an aperture (not shown) configured on the upper side of the cassette handler. The cassette handler 502 is configured to fit into the detection device 500 so that at least a portion of the aperture is aligned with an electromagnetic radiation detector 503 of the detection device. The radiation detection device 500 also includes signal processing components 504, a printer 505, a user interface screen 506, and other obvious components and capabilities required to use the disclosed invention.

The disclosed detection device also includes a detection component comprising a self-calibrating Sensor IC with a discrete detection region, a charge-coupled device, an electro-optical sensor, a photodetector, a photodiode, a photomultiplier tube, a single-photon avalanche diode and a visible light photon counter. The detection device is configured to (1) detect electromagnetic radiation generated as a result of a chemical reaction occurring on a cassette device; (2) convert the electromagnetic radiation into an electrical signal; (3) process the electrical signal to determine whether MRSA is present or absent in the sample; and (4) communicate whether MRSA is present or absent in a sample after the signal is processed. The detection device may also be configured to communicate data to one or more additional devices. The components and various configurations thereof required to carry out these operations are known to those skilled in the art.

Figure 6:
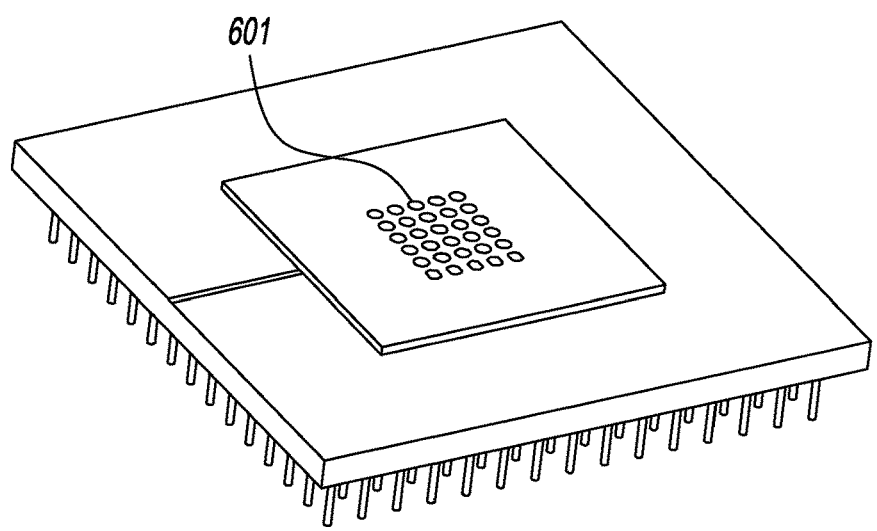
FIG. 6 depicts a self-calibrating sensor integrated chip photodiode array 601 of an electromagnetic radiation detection device.
Figure 7:
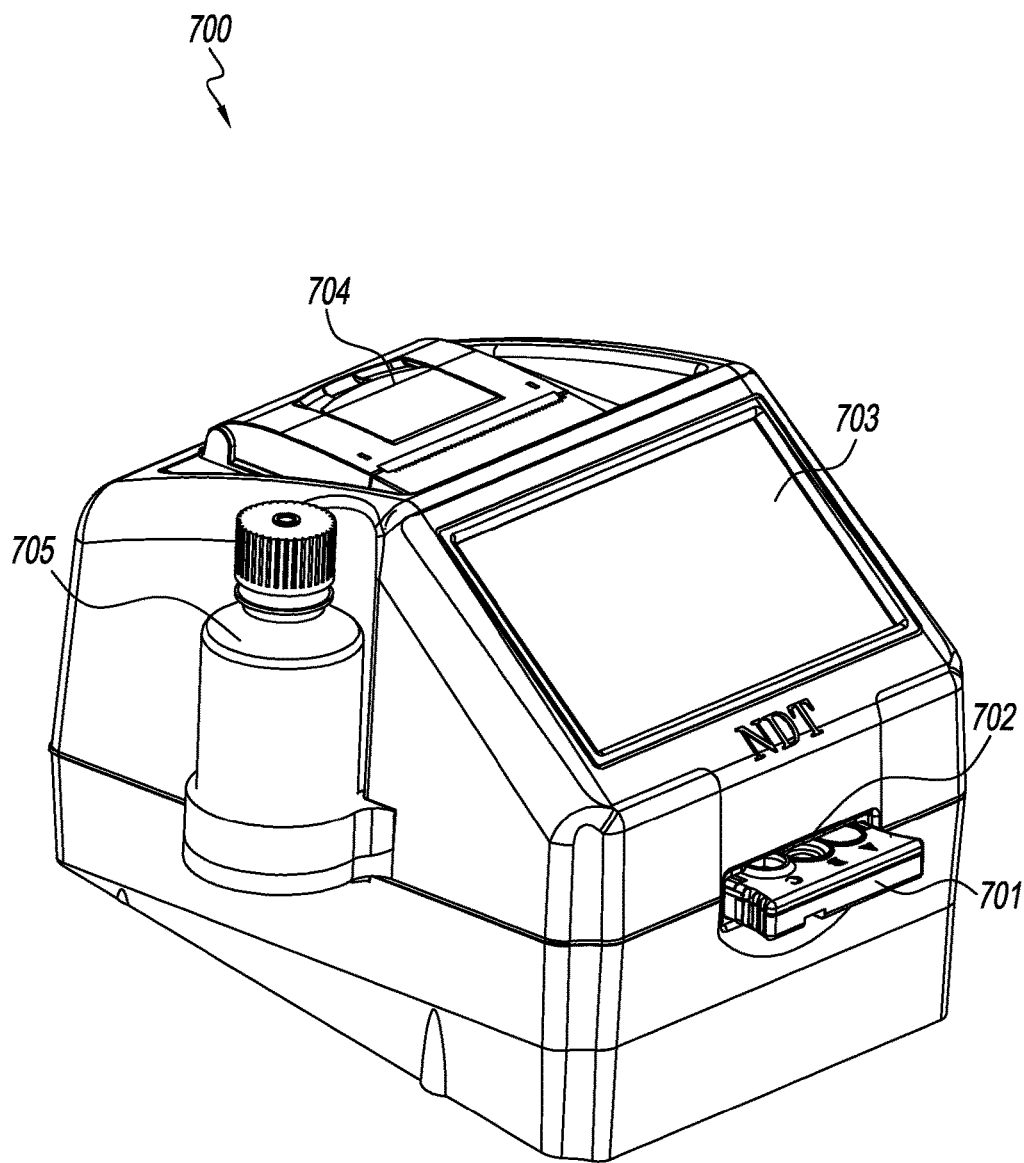
FIG. 7 depicts an assembled Sensor IC radiation detection device 700 comprising a test cassette 701, a cassette opening 702, a user interface screen 703, a printer 704, and a luminol bottle 705.

With reference to FIG. 6, the Sensor IC 601 is comprised of an array of 25 individual diodes, each capable of independently detecting a minimum luminous flux of 200,000 photons per second, and seven orders of magnitude of light intensity variation. Each diode of the Sensor IC may be independently biased, and the detected analog signals independently read by the user interface. Because of the sensitivity of the diodes, and because of manufacturing variabilities within the integrated chip, the Sensor IC must receive two levels of calibration to allow effective operation. Upon initial production, each diode will produce a different electrical signal value in response to zero photon strikes, or dark condition. The device accordingly includes integrated chips that deliver small amounts of direct current (DC) voltage (microvolt scale) to each diode so that all 25 diodes produce identical signals in response to the dark condition. In addition, at initial production the Sensor IC diodes also produce different electrical signals in response to exposure to the same number of photons per second (intensity). Therefore, a first order linear regression is performed on the outputs of each of the 25 diodes, and coefficients are calculated for each diode to enable the diodes to produce identical signals in response to a dark and a light condition. The device then stores the calculated coefficients. During operation, the detection device applies the stored calibration coefficients to each diode measurement, thereby allowing the Sensor IC to self-calibrate each photodiode independently. When the disclosed cassette device is inserted into the detection device and properly aligned, each aperture will correlate with 3 diodes on the Sensor IC, providing the detection device with redundant measurements for each sample region.

In various embodiments, the disclosed invention also includes a method for analyzing a sample, including the following processes: providing a sample; placing the sample in at least one sample preparation basin on a cassette device; mixing the sample and applying the sample to a lateral flow strip through a sample well; inserting the cassette device into a Sensor IC device; using a luminous reagent delivery device to add luminol to a cassette device through a luminol well. The luminol migrates into the test strip reaction zone and reacts with the sample fluid, wherein the Sensor IC device detects the presence or absence of MRSA in the sample.

In the disclosed method, a sample of fluid potentially containing MRSA is taken by applying a standard cotton swab to the inside of the first 1 to 2 mm of an individual's nasal cavity and placing the sample in a specimen tube containing a growth medium, such as Trypticase soy broth. Once placed in the growth medium, the specimen tube is tightly capped and incubated for at least 16 hours, and no more than 30 hours, at 37° C. in a heat block. The disclosed method of sample treatment differs from typical hospital laboratory practice in that specimens are usually loosely capped, and hospital incubators are normally used to incubate the sample.

An extraction reagent comprised of NaOH and buffering agents is added to Basin A, and a neutralization reagent comprised of a solution of dilute HCl and buffering agents is added to Basin B. A syringe is used to take up the entire sample from the specimen tube, and a 0.2 micron filter is placed onto the syringe; the sample is then expelled through the filter into Basin A. Then the extraction reagent in Basin A is drawn through the filter into the syringe with the sample, where it breaks down any MRSA that is present. Then all of the liquid in the syringe is expelled through the filter into Basin B. This pushes any PBP2a present in the sample into Basin B. At this point, a monoclonal PBP2a antibody conjugated with HRP is added to Basin B. A pipette is then used to extract the entire contents of Basin B and place them into sample well C.

The liquid sample will flow onto the sample acceptor pad and then downstream onto the lateral flow strip. The sample will continue to flow downstream toward the reaction zone, where it will interact with the sample capture region, which is a portion of the lateral flow strip containing a monoclonal MRSA PBP2a antibody. Some of the HRP conjugated with PBP2a will bind to the PBP2a antibody in the capture region, and unbound HRP conjugated antibody will then flow downstream along the lateral flow strip to a negative control region, and will continue toward the positive control region. The positive control region is treated with IgG antibody specific for murine antibodies. Unbound HRP conjugated antibody will be captured at the positive control region. The cassette is then inserted into the cassette handler, which is located within the Sensor IC detection device. A luminous reagent delivery device then introduces luminol into the luminol channel that is located on the upper surface of the cassette device. The luminol flows down the channel to a luminol well in the cassette device, and flows through the luminol well and onto the luminol acceptance region of the lateral flow strip. The luminol flows downstream along the lateral flow strip to the reaction zone, where it reacts with the HRP trapped in the capture region and the positive control region, and produces electromagnetic radiation. The electromagnetic radiation is transmitted through a row of three apertures in the upper portion of the cassette device and positioned directly above the sample capture region, the negative control region and positive control region. The cassette handler guides the cassette into a position in which the cassette openings are aligned with electromagnetic radiation detectors of the detection device. A door prevents the entry of interfering light into the detection device. The cassette is stabilized in position by four hemispherical ball detents (located approximately at the corners of the underside of the cassette) that interact with four spring-mounted ball plungers of the cassette handler. The electromagnetic radiation produced in the sample capture region, and control regions is then detected by the radiation detection device, and electrical signals are produced in response to the detection. The electrical signals are calibrated and then processed by a processor located within the detection device. A signal is then generated indicating a valid or invalid test, and if the test is valid, the device generates a signal indicating the presence or absence of MRSA PBP2a and communicates to both the user interface screen and printer, where a message is printed and made available for use by a user.

The disclosed invention also includes a method of using a Sensor IC detection device in which a sample is analyzed by providing a test format which includes a sample capture signal, a positive control signal, and a negative control (background) signal to the detector device. Because the detector device has 25 discrete photodiodes, and a single sample tested according to the disclosed test format uses 9 diodes, the test format may potentially be expanded to include multiple analytes. Accordingly, the disclosed test format and Sensor IC device could allow accurate testing of up to 7 analytes simultaneously.

The disclosed invention also includes a method for analyzing a sample, including detecting electromagnetic radiation emitted from the cassette device using the detection device.

The method further includes detecting the presence or absence of MRSA in a sample, utilizing any of the cassette, cassette handler, or the detection device, according to the disclosed methods.

The arrangements and descriptions related above are example embodiments only, and other obvious configurations and applications are included within spirit of the disclosed invention. The disclosed invention is in no way limited to the methods and materials described. These examples serve to illustrate that although the specification herein does not list all possible device features or arrangements or methods for all possible applications, the invention is broad and may incorporate other useful methods or aspects of materials, devices, or systems or other embodiments, which are readily understood and obvious for the broad applications of the present invention.

This has been a description of the present invention along with a preferred method of practicing the present invention, however the invention itself should only be defined by the appended claims.

What is claimed is:

1. A cassette device for determining the presence or absence of Methicillin-resistant *Staphylococcus aureus* ("MRSA") in a sample, comprising:
   (a) a lateral flow strip, comprising (1) a sample acceptor pad for receiving a liquid sample mixed with an enzyme conjugate, (2) a region for accepting a luminous reagent, (3) a region comprising a reaction zone, wherein the reaction zone includes a substance binding region, a negative control region and a positive control region, and (4) an absorbent pump, and wherein (i) the sample acceptor pad, the region for accepting a luminous reagent, the reaction zone, and the absorbent pump are in fluid communication, and facilitate fluid flow in a downstream direction from the sample acceptor pad to the absorbent pump; (ii) the substance binding region includes an antibody for capturing a component of MRSA; (iii) the positive control region includes an antibody for capturing the enzyme conjugate, and (iv) the enzyme conjugate is capable of binding with the component of MRSA and reacting with the luminous reagent, thereby generating electromagnetic radiation; and (b) a housing, comprising (1) an upper component comprising a first basin for sample preparation, a second basin for sample preparation, a first well for adding a sample, a second well for adding a luminous reagent, a luminous reagent receiving area, a plurality of apertures to allow electromagnetic radiation generated on the lateral flow strip to escape the cassette device wherein the plurality of apertures includes a first aperture corresponding to the substance binding region, a second aperture corresponding to the negative control region, and a third aperture corresponding to the positive control region, a transparent adhesive seal covering the plurality of apertures, the second well, and partially covering the luminous agent receiving area, a plurality of latch receiving regions, a plurality of pressure tabs to contact the lateral flow strip, and a plurality of alignment guides to secure the lateral flow strip in place; (2) a lower component comprising a region upon which the lateral flow strip rests, a sample reservoir, a plurality of alignment guides to secure the lateral flow strip in place, a plurality of latches located complimentary to the latch receiving regions on the upper housing and capable of exerting positive pressure to mechanically latch the upper component and the lower component together, and a plurality of detents for mechanically securing the cassette device in a cassette handler device; (3) an identification label configured to allow electronic identification of the cassette device; and wherein (i) the first well and second well are in fluid communication with the lateral flow strip; (ii) the first well includes a three-sided guide configured to contact the lateral flow strip and direct a flow of sample in the downstream direction; (iii) the luminous agent receiving area includes a first nipple configured to receive the luminous reagent, a channel for transporting the luminous reagent from the nipple to the second well, wherein a surfactant at least partially coats the channel, and a second nipple configured to cause a droplet of luminous reagent to contact the lateral flow strip; and (iv) the apertures include shielding structures configured to direct electromagnetic radiation out of the apertures.

2. The cassette device of claim 1, wherein the antibody for capturing the component of MRSA is a Penicillin Binding Protein 2a ("PBP2a") monoclonal antibody.

3. The cassette device of claim 1, wherein the enzyme conjugate comprises horseradish peroxidase ("HRP").

4. The cassette device of claim 3, wherein the antibody for capturing the enzyme conjugate is an IgG antibody.

5. The cassette device of claim 1, wherein the luminous reagent is luminol.

6. The cassette device of claim 1, wherein the lateral flow strip is configured so that one or more of the following are partially or completely overlapping: the sample acceptor pad, the region for accepting a luminous reagent, the reaction zone, and the absorbent pump.

* * * * *